(12) United States Patent
Babcock et al.

(10) Patent No.: US 9,581,569 B2
(45) Date of Patent: Feb. 28, 2017

(54) METHOD FOR MEASURING BACTERIAL GROWTH AND ANTIBIOTIC RESISTANCE USING SUSPENDED MICROCHANNEL RESONATORS

(75) Inventors: Kenneth Babcock, Santa Barbara, CA (US); Scott R. Manalis, Cambridge, MA (US)

(73) Assignee: Affinity Biosensors, LLC, Santa Barbara, CA (US)

( * ) Notice: Subject to any disclaimer, the term of this patent is extended or adjusted under 35 U.S.C. 154(b) by 222 days.

(21) Appl. No.: 13/348,809

(22) Filed: Jan. 12, 2012

(65) Prior Publication Data

US 2012/0174657 A1    Jul. 12, 2012

Related U.S. Application Data

(60) Provisional application No. 61/461,112, filed on Jan. 12, 2011.

(51) Int. Cl.
*G01N 29/036*    (2006.01)
*G01N 29/02*    (2006.01)

(52) U.S. Cl.
CPC ......... *G01N 29/036* (2013.01); *G01N 29/022* (2013.01); *G01N 2291/0256* (2013.01); *G01N 2291/0427* (2013.01)

(58) Field of Classification Search
None
See application file for complete search history.

(56) References Cited

U.S. PATENT DOCUMENTS

| 8,631,685 B2* | 1/2014 | Manalis ................. G01N 15/00 73/61.71 |
| 8,815,177 B2* | 8/2014 | Perroud et al. ............... 422/503 |
| 2009/0044608 A1* | 2/2009 | Babcock et al. ............. 73/64.53 |
| 2010/0227310 A1* | 9/2010 | Manalis et al. ................... 435/5 |

* cited by examiner

*Primary Examiner* — Robert R Raevis
(74) *Attorney, Agent, or Firm* — Mark Rodgers

(57) ABSTRACT

Methods for improving measurements of bacterial growth, such as mass, in Suspended Microchannel Resonators (SMR's). Methods include techniques to provide for bacterial growth over time in response to changing fluid environment to aid in determining parameters such as drug resistance and drug susceptibility. In particular the methods include trapping multiple bacteria in the SMR for a time period and varying the fluid to include sequences of nutrients and antibiotics, and measuring the rate of mass change of the bacteria in response to the changes in fluid composition.

7 Claims, 4 Drawing Sheets

METHOD FOR MEASURING BACTERIAL GROWTH AND ANTIBIOTIC RESISTANCE USING SUSPENDED MICROCHANNEL RESONATORS

RELATED APPLICATIONS

This application claims priority to U.S. provisional application 61/461,112, filed Jan. 12, 2011

FEDERALLY SPONSORED RESEARCH

N/A

BACKGROUND OF THE INVENTION

This invention relates to methods for measuring bacterial growth and antibiotic resistance, and particularly to such measurements using a Suspended Microchannel Resonator (SMR) and measuring the mass of multiple bacteria over time and in changing fluidic environments.

Precision measurements of nanometer- and micrometer-scale particles, including living cells and multicellular entities such as bacteria, have wide application in pharmaceuticals/drug delivery and disease studies, as well as in other major industries and fields of research. This need is growing due to the need to better understand and treat diseases and develop and maintain effective treatments and drugs.

A variety of particle sizing and counting techniques, such as light scattering, Coulter Counters and others are known in the art. These techniques are embodied in commercial instruments and are used in industrial, medical, and research applications. Although such techniques have proven utility, they have limitations that limit their applicability. Relatively recently, particle detection and measurement based on the use of SMR's has been developed, and shows promise of going beyond some of the limitations of conventional techniques. The SMR uses a fluidic microchannel embedded in a resonant structure, typically in the form of a cantilever or torsional structure. Fluids, possibly containing target particles, are flowed through the sensor, and the contribution of the particles to the total mass within the sensor causes the resonance frequency of the sensor to change in a measurable fashion. SMR's are typically microfabricated MEMS devices. The use of microfabricated resonant mass sensors to measure fluid density has been known in the literature for some time [P. Enoksson, G. Stemme, E. Stemme, "Silicon tube structures for a fluid-density sensor", Sensors and Actuators A 54 (1996) 558-562]. However, the practical use of resonant mass sensors to measure properties of individual particles and other entities suspended in fluid is relatively recent, as earlier fluid density sensors were not designed to measure individual particles at the micron and submicron scale.

In a body of work including work by the inventors of this application, miniaturization and improvement of several orders of magnitude in mass resolution has been demonstrated. Development in the microfabrication recipes, the fluidics design, and measurement techniques are described in a number of co-pending patent applications and scientific publications. In particular U.S. patent application Ser. Nos. 11/620,320, 12/087,495, and 12/305,733 are particularly relevant and are incorporated by reference in their entirety. Also of relevance is a publication by others including the current inventors, [T. P. Burg, M. Godin, S. M. Knudsen et al., "Weighing of biomolecules, single cells and single nanoparticles in fluid," Nature 446 (7139), 1066-1069 (2007)] By using the microfabrication techniques described in the references, SMR sensors have been fabricated with mass resolution of less than 1 femtogram ($10^{-15}$ g). This resolution is sufficient to detect and measure the mass of individual particles in the range of –100 nanometers up to many microns in size, including living cells.

Improvements in SMR based measurement techniques have been disclosed, which allow for a particle to be held in the measurement portion of the SMR for extended periods of time. Although the disclosed techniques have the advantage of improving signal to noise, they also provide for the ability to measure particle properties which may change over time. Of particular interest is the possibility of measuring cell or bacterial growth. High precision measurements of the mass of living cells or small multi-cellular organisms such as bacteria have not been possible previously.

Given the mass resolution of current SMR's cell mass measurements may be accomplished with resolution approximately 1% of the mass of a typical bacterium, which is sufficient to measure mass change due to growth and/or mitosis. With such resolution it is possible to detect bacterial growth by measuring change in mass over time, and potentially even more importantly to measure bacterial response to changes in the chemical or environmental properties of the bacteria's liquid environment. Such measurements would have applicability in drug resistance/susceptibility studies, and general environmental toxicity studies. More than 100,000 deaths per year in the US result from bacterial infections, behind only cancer and heart disease. Moreover the rising resistance of bacteria to existing antibiotics coupled with the difficulty in developing new antibiotics is negatively impacting effective treatment of bacterial infections. One of the leading roadblocks to analysis of bacterial resistance to existing drugs and the effectiveness of new drugs is the slowness of existing bacterial assay techniques, such as disk diffusion/dilution assays, which commonly take days to produce results. Therefore it is the object of this invention to provide faster, accurate bacterial assays based on the application of SMR's.

SUMMARY OF THE INVENTION

The invention, in one embodiment, is a Method for measuring bacterial growth using an SMR with a particle trap, including introducing at least two bacteria into the SMR in a fluid medium, trapping the bacteria in the particle trap, controlling the trapping time and fluid environment to which the bacteria are exposed, and measuring the mass and growth rate of the bacteria during the period when bacteria are trapped.

In some embodiments the method includes changing the properties of the fluid, including, chemical and environmental properties, during the period the bacteria are trapped in the SMR.

In another embodiment, the method of includes measuring the change in growth rate over time in response to the change in fluid properties. From these measurements drug resistance and drug susceptibility can be determined. In a particular embodiment the method includes changing the fluid environment in a sequence of collection, growth and antibiotic exposure steps.

In a preferred embodiment, the growth step includes exposure to nutrient in the fluid and the antibiotic exposure step includes exposure to a series of different antibiotics to determine which ones are effective at inhibiting bacteria growth. In addition changes in mass due to nutrient efficiency as well as gas absorption may be measured.

BRIEF DESCRIPTION OF THE DRAWINGS

The invention will be better understood by referring to the following figures.

DETAILED DESCRIPTION OF THE INVENTION

The embodiments described herein are improved methods that can be implemented using the microfabrication techniques, fluidics, and control electronics disclosed in the documents referenced and other publications available at the time the invention was made. Since those aspects of the invention do not contribute to the novelty, they are not described in detail. For instance novel versions of the SMR's may be produced with mask changes in the microfabrication process. Similarly the fluidics, data acquisition, and data processing steps can be accomplished with implementations derived from set-ups previously disclosed. The novelty of the current invention lies in the arranging of the physical SMR geometries, fluid control schemes and measurement steps to achieve significantly improved results. Also the term particle is interchangeably used in this application to mean any particulate substance, including cells and bacteria and particularly live cells or bacteria in a suitable fluid medium. Also it is to be understood that fixed end cantilever SMR's are shown by way of example, but the techniques disclosed are not restricted to any particular SMR geometry.

Techniques for trapping of particles in SMR's and measuring changes in the particle characteristics over time in response to changes in the carrier fluid medium are discussed in detail in co-pending Application U.S. Ser. No. 12/661,772, whose contents are incorporated in their entirety by reference. In particular, microfabricated SMR's configured with particle traps sized to trap cellular dimensioned particles are disclosed. Fluidic systems suitable for injecting fluids carrying cellular sized objects into the SMR fluidics channels and varying the fluid composition over time are also discussed. However the disclosure of the '772 application was primarily directed toward the trapping and characterization of single particles such as human cells.

A single bacterium may be trapped using trapping geometries within the design rules of current SMT fabrication. However, the growth and/or mitosis rate of single cells is slow so measurable changes in a single bacterium may require long measurement times.

Figure 1:
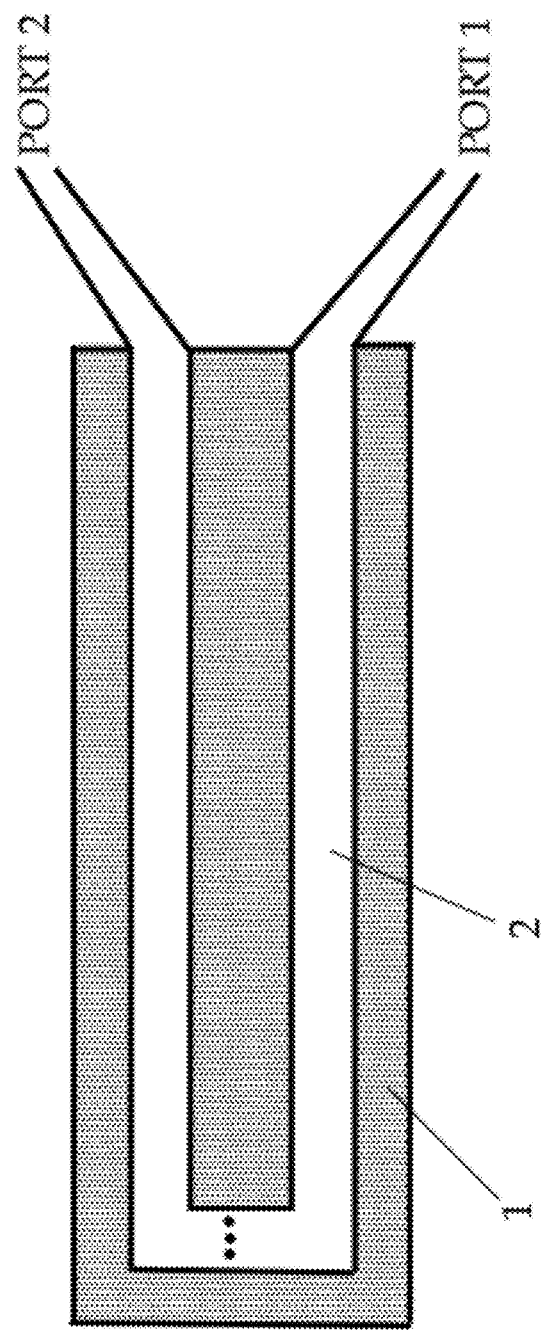
FIG. 1 is a schematic illustration of a Suspended Microchannel Resonator configured with a particle trap particularly suitable to the invention.

To speed up characterization times of trapped bacteria, multiple bacteria may be trapped at one time, so the cumulative growth rate becomes measurable on much shorter time scales. Although many of the trap geometries disclosed in the '772 application would work, as well as others which will occur to those skilled in the art, the inventors have found that the trap geometry shown in FIG. 1 is particular suitable for trapping multiple bacteria. FIG. 1 shows a typical single channel 2, two port cantilever SMR 1 with fluid inlet PORT 1 and outlet PORT 2. In this embodiment the trap consists of one or more posts or sieves spanning a dimension of channel 2, preferably at the free end of the lever, which is the most sensitive measurement location. Using MEMS techniques, posts can be fabricated to have spacings 500 nanometers or less, which is sufficiently small to prevent the passage of particles or cells, while still allowing the suspending fluid to flow freely by the posts and any trapped particles.

Figure 2:
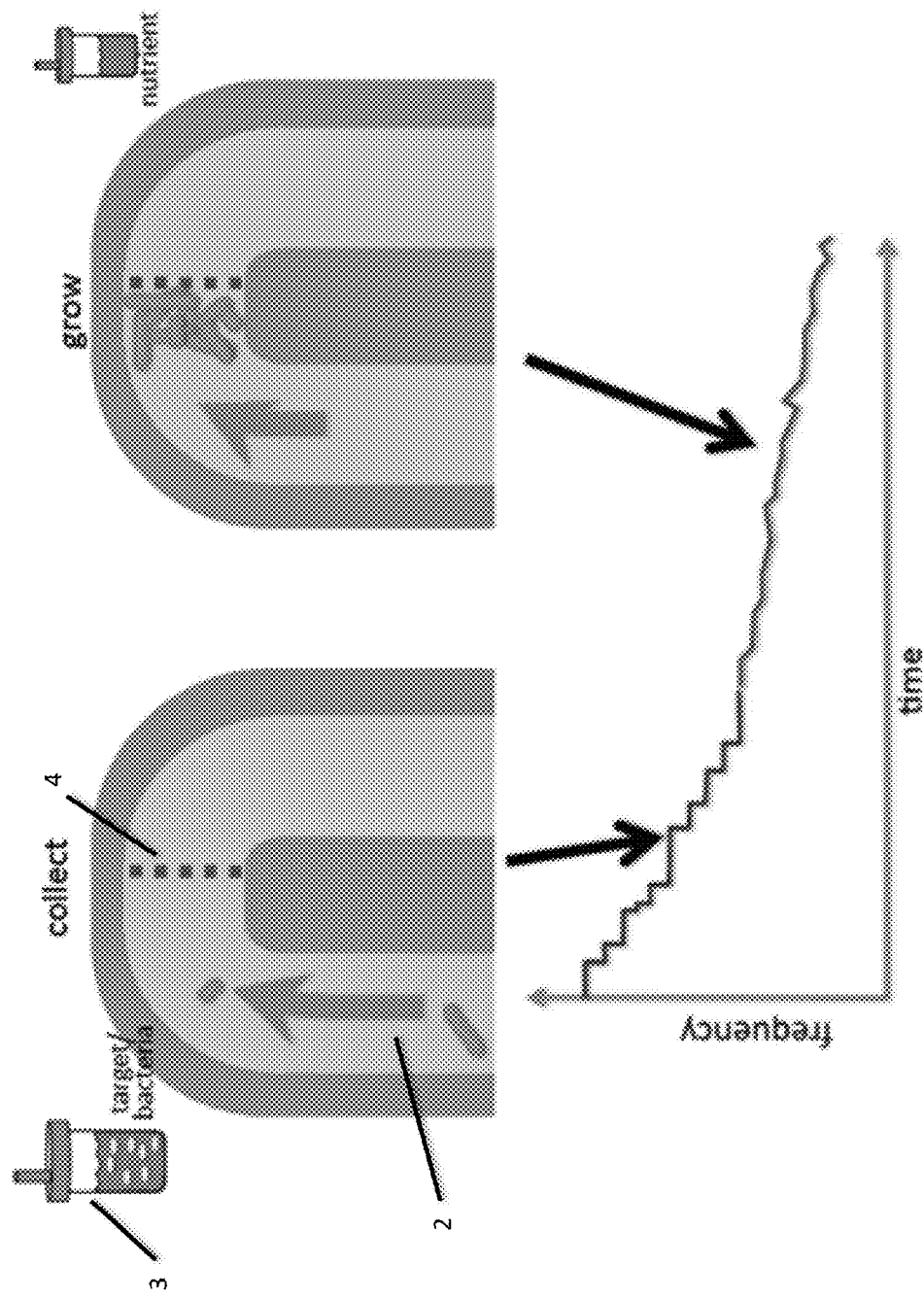
FIG. 2 depicts the trapping of multiple bacteria in an SMR trap.

FIG. 2 depicts the application of a trapping SMR to bacteria characterization. A fluid containing a fixed amount of target bacteria 3 is injected onto channel 2. The entry of a bacterium into the trap region 4 will increase the mass of the SMR and cause a downward step in the resonant frequency. By counting the number of downward steps in the frequency signal the number of trapped bacteria will be known, and any desired number of bacteria can be captured. Once the desired number are trapped, the source solution can be switched to a pure fluid containing no bacteria. This fluid may include nutrient, and growth and/or mitosis of the trapped bacteria will commence. If a sufficiently large number of bacteria are trapped, the change in bacterial mass vs. time will be observable as a rapid decrease in the resonant frequency. This decrease occurs as the trapped bacteria extract nutrient material from the environment and add it to their mass, and also as they increase their numbers as they undergo mitosis. Experiments by the authors have shown that with 10-100 bacteria the growth rate can be measured within a few seconds. Of course these steps do not have to be cleanly delineated. For instance the nutrient could be present from the beginning if the collection is rapid.

Figure 3:
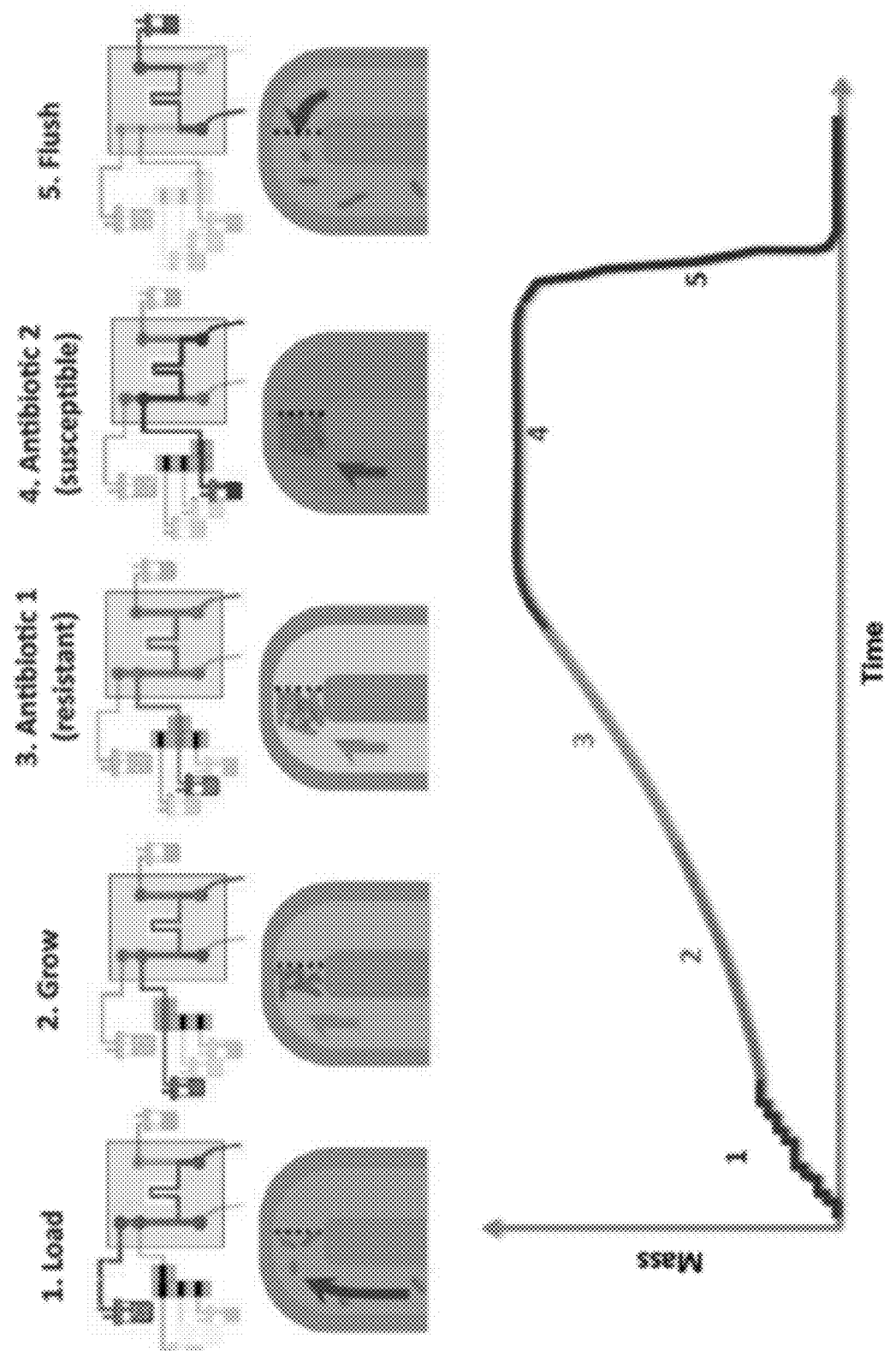
FIG. 3 is a schematic illustration of a preferred embodiment of the invention.

FIG. 3 depicts the system of FIG. 2 set-up and operating to do a true bacterial assay of a type that provides similar information to existing assay techniques, albeit at very much reduced time. A desired number of bacteria are collected at the trap in the load phase. Once collection is stabilized a growth phase may be induced to witness mass change under benign conditions, to characterize normal growth. Then a series of antibiotics may be introduced sequentially or in treatment "cocktails" to compare the effect of the antibiotics on growth compared to the normal growth observed in the growth phase. Both antibiotics that are known or suspected to have reduced effectiveness, as well as ones believed to be effective, may be introduced in sequence leading to complete information for clinicians and researchers. Thus bacterial resistance and susceptibility may be observed. A system flush step may also be used between measurement cycles to expel the bacteria and sterilize the SMR.

The inventors have observed load, growth, and antibiotic exposure times of less than 10 minutes total. In some real-world drug susceptibility applications, the total time for a sequence such as that shown in FIG. 3 may take about an hour. This is far faster than conventional methods such as broth cultures or disk diffusion techniques, which require a culture to mature for many hours or even a day or more to produce results.

Figure 4:
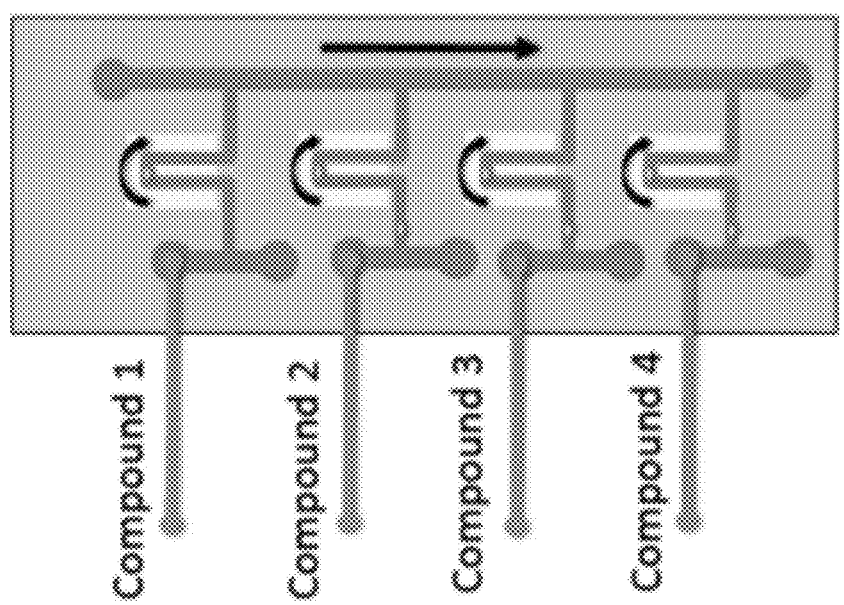
FIG. 4 is a schematic illustration of an array of Suspended Microchannel Resonators configured for rapid bacterial assay.

Times could be even further reduced by fabricating arrays of SMR's, as shown in FIG. 4, allowing for simultaneous exposure to multiple antibiotics and/or nutrients at once.

With minor variations the invention can also be used in other applications which require precise measurement of cell growth. For example, cell and bacteria cultures are widely employed to manufacture quantities of target proteins to be used in drug formulations. These "drug factory" cultures are precisely engineered to optimize the growth rate of the cell culture so as to maximize yield of the protein product. Using the invention, the cell growth rate could be measured as a function of changes in nutrient content or concentration, or as a function of changes to other environmental parameters such as absorbed oxygen. In this way the optimal culture growth parameters could be determined and monitored.

The foregoing description of the embodiments of the present invention has shown, described and pointed out the fundamental novel features of the invention. It will be understood that various omissions, substitutions, and changes in the form of the detail of the systems and methods as illustrated as well as the uses thereof, may be made by those skilled in the art, without departing from the spirit of the invention. Consequently, the scope of the invention should not be limited to the foregoing discussions, but should be defined by appended claims.

What is claimed is:

1. A method for measuring bacterial growth using an SMR with a microfabricated particle trap, comprising;
   using an SMR with a microfabricated particle trap, wherein the trap is designed and fabricated with trap geometries sized to trap cellular dimensioned particles,
   introducing at least two or more bacteria cells of a size trappable by the particle trap into the SMR in fluid up to a predetermined desirable number by counting incremental resonant shifts associated with each introduced bacteria cell,
   trapping the bacteria in the particle trap wherein the bacteria are held in the trap for a period of time,
   controlling the fluid environment in the SMR while the bacteria are held in the trap; and,
   measuring the change in mass of the trapped bacteria due to a combination of cell growth and replication during the period when bacteria are held in the trap.

2. The method of claim 1 further comprising changing the properties of the fluid, including, chemical and environmental properties, during the period the bacteria are trapped in the SMR.

3. The method of claim 2 further comprising;
   determining from the change in mass over time in response to the change in fluid properties, parameters comprising;
   drug resistance;
   drug susceptibility.

4. The method of claim 2 further comprising changing the fluid environment in a sequence of growth and antibiotic exposure steps.

5. The method of claim 4 wherein the growth step includes exposure to nutrient in the fluid and the antibiotic exposure step includes exposure to at least one antibiotic.

6. The method of claim 1 further comprising;
   determining nutrient efficacy from the change in mass over time.

7. The method of claim 1 further comprising;
   determining from the change in mass over time the bacteria's absorption of gas present in the fluid.

* * * * *